US008336554B1

(12) United States Patent
Williams

(10) Patent No.: US 8,336,554 B1
(45) Date of Patent: Dec. 25, 2012

(54) LOWER LEG AND FOOT STABILIZER

(76) Inventor: Michael A. Williams, Oakboro, NC (US)

(*) Notice: Subject to any disclaimer, the term of this patent is extended or adjusted under 35 U.S.C. 154(b) by 520 days.

(21) Appl. No.: 12/571,462

(22) Filed: Oct. 1, 2009

(51) Int. Cl.
 *A61F 5/37* (2006.01)
(52) U.S. Cl. .............. 128/882; 128/845; 602/12; 5/648; 5/649; 5/650; 5/651
(58) Field of Classification Search .............. 128/105.1, 128/845, 846, 869, 870, 877, 878, 882; 36/136, 36/140; 297/466, 464; 211/59.1; 5/655, 5/657, 658, 659, 660, 661, 662, 648, 649, 5/650, 651; 280/250.1, 647, 650; 602/19, 602/26, 27, 28, 29
See application file for complete search history.

(56) References Cited

U.S. PATENT DOCUMENTS

| D259,675 | S | 6/1981 | Gordon et al. |
| 4,461,288 | A | 7/1984 | Curtis |
| 4,649,939 | A | 3/1987 | Curtis |
| 5,524,640 | A * | 6/1996 | Lisak et al. ........................ 5/655 |
| 5,533,950 | A | 7/1996 | Lochbaum |
| D380,267 | S | 6/1997 | Roth |
| 5,645,525 | A | 7/1997 | Krivosha |
| 5,755,679 | A | 5/1998 | Selner et al. |
| 6,115,857 | A | 9/2000 | Bidegain |
| 6,594,922 | B1 | 7/2003 | Mansfield et al. |
| 7,066,547 | B1 | 6/2006 | Russell et al. |
| 7,171,766 | B2 | 2/2007 | Bouche et al. |
| D540,950 | S | 4/2007 | Johnson |
| 7,334,275 | B1 | 2/2008 | Kirkwood |
| 7,354,110 | B1 | 4/2008 | Raghubir |
| 2007/0216094 | A1 * | 9/2007 | Sidhu ............................ 273/275 |
| 2009/0012437 | A1 * | 1/2009 | Tucker et al. .................... 602/19 |
| 2010/0163059 | A1 * | 7/2010 | Tierney et al. ................ 128/876 |

FOREIGN PATENT DOCUMENTS

WO   WO2006/134363 A2 * 12/2006

\* cited by examiner

*Primary Examiner* — Justine Yu
*Assistant Examiner* — Raymond E Harris
(74) *Attorney, Agent, or Firm* — Montgomery Patent & Design LLC; Robert C. Montgomery; Joe Yaksich

(57) ABSTRACT

A device to hold one's foot in a neutral position while sitting in order to aid in healing includes a large plastic panel with a set of parallel plastic strips extending upward. These strips are adjustable upon the surface of the board using a series of small holes and corresponding pins. The strips are thus aligned to match the width of one's foot being held in a shoe. When aligned upon the floor, the foot, in a normal shoe without the use of a brace, is held in a neutral position which helps prevent contracture of the leg and foot muscles thus promoting faster healing after surgery. Additionally, the current device does not provide for pinching or twisting as commonly occurs with conventional prosthetic braces.

13 Claims, 5 Drawing Sheets

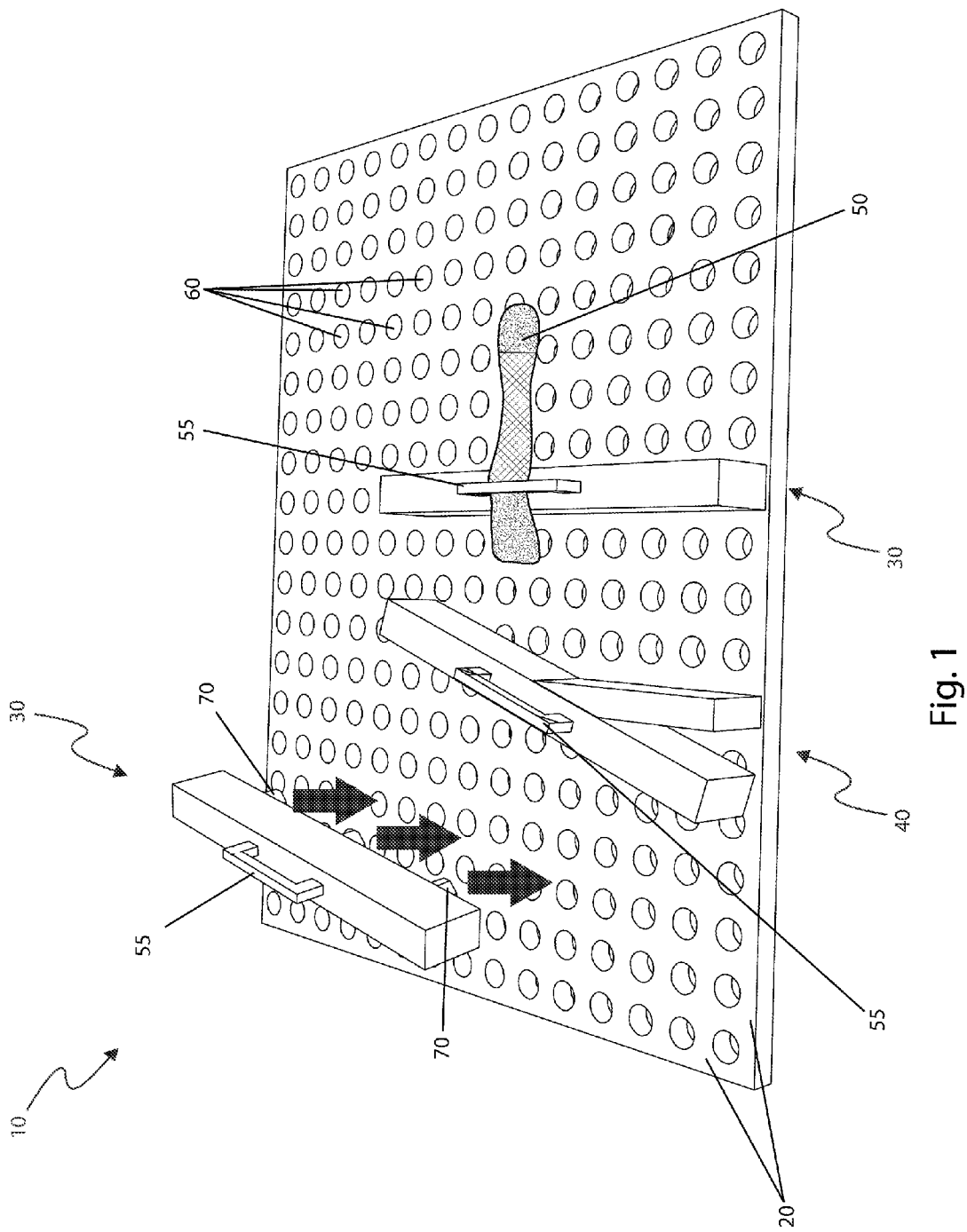

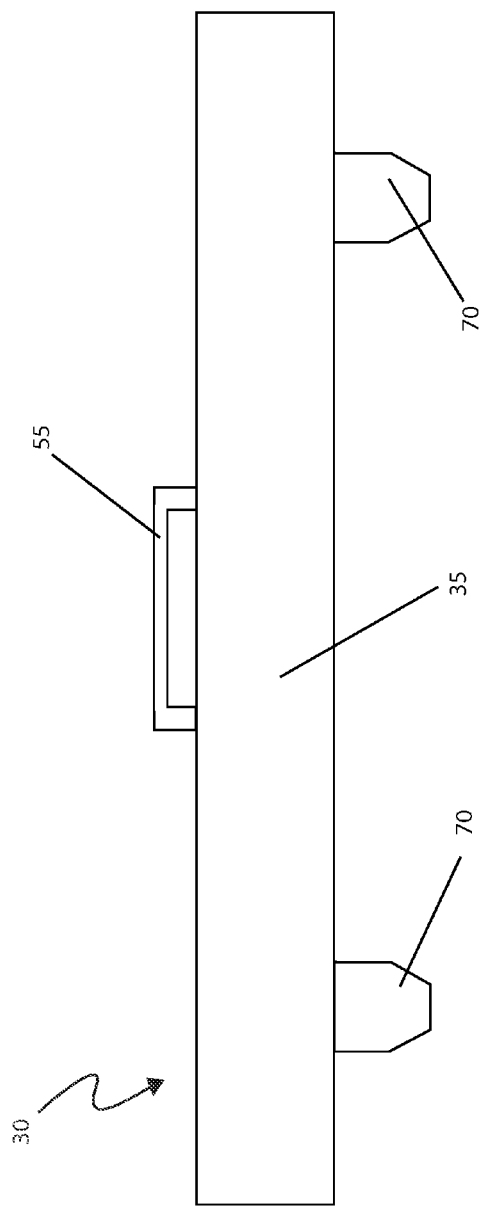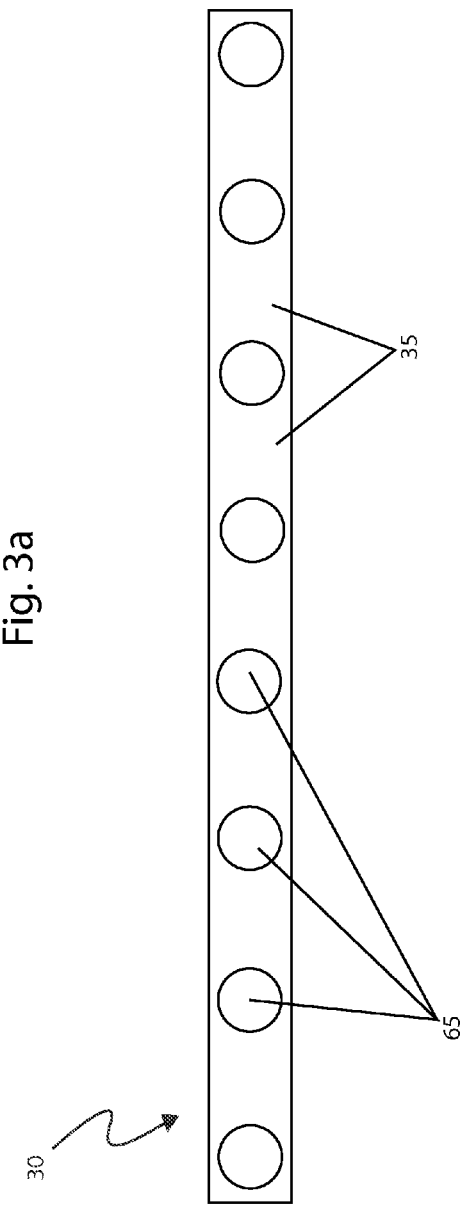

LOWER LEG AND FOOT STABILIZER

RELATED APPLICATIONS

The present invention was first described in a notarized Official Record of Invention on Jun. 9, 2008, that is on file at the offices of Montgomery Patent and Design, LLC, the entire disclosures of which are incorporated herein by reference.

FIELD OF THE INVENTION

The present invention relates generally to post-surgical recovery practices, and in particular, to a device for aiding in the stabilization of the lower leg and foot to expedite the post-surgical healing process.

BACKGROUND OF THE INVENTION

Thousands of persons a year undergo surgery on their feet or legs. Many of these procedures are rather serious, resulting in a temporary loss of function and mobility. Many common devices, such as prosthetic leg braces, are used in an attempt to expedite the healing process. However, many such devices are known to cause problems such as pinching, binding, and other nuisances. Such discomforts prompt the user to respond to unpleasant stimuli in a way that is detrimental to the recovery effort. For instance, pinching may prompt the wearer to twist their leg, when keeping the leg in a neutral position is most advantageous.

Various attempts have been made to provide for a means to secure the foot and lower leg in a neutral position to aid in recovery. Examples of these attempts can be seen by reference to several U.S. patents. U.S. Pat. No. 5,645,525, issued in the name of Krivosha, describes a device and method for stabilizing the heel of a patient. The Krivosha device encompasses the user's ankle area, thereby limiting the field of motion. U.S. Pat. No. 7,066,547, issued in the name of Russell et al., describes a portable foot rest with a stabilizing means. Devices such as the Russell device provide the user a stable platform for a foot to rest upon which can be oriented in a comfortable manner.

Additionally, ornamental designs for foot and leg stabilizing devices exist, particularly U.S. Pat. Nos. D 259,675, D 380,267, and D 540,950. However, none of these designs are similar to the present invention.

While these devices fulfill their respective, particular objectives, each of these references suffer from one or more disadvantages. Many of these devices are prone to discomforts, such as shifting, pinching, or binding. Also, many of these devices do not provide for a means to discourage unnecessary movement of the lower leg. Furthermore, many of these devices function in a manner that encourages the user to avoid discomfort by moving in a way which is detrimental to the recovery process. Accordingly, there exists a need for a foot and lower leg stabilizing device without the disadvantages as described above. The development of the present invention substantially departs from the conventional solutions and in doing so fulfills this need.

SUMMARY OF THE INVENTION

In view of the foregoing references, the inventor recognized the aforementioned inherent problems and observed that there is a need for a device that provides the user with stability for a foot and lower leg in a manner that is comfortable, simple, and which does not encourage detrimental movement on the part of the user. Thus, the object of the present invention is to solve the aforementioned disadvantages and provide for this need.

To achieve the above objectives, it is an object of the present invention to provide a board adapted to be placed on the ground while the patient is seated. This board contains a plurality of apertures that are arranged in an evenly spaced matrix of columns and rows, and which are intended for use in securing the foot rails.

Another object of the present invention is to provide a plurality of rails with integral anchors which are removably attached to the board. These rails also include a plurality of apertures intended for use in securing the rails to the board, in a manner which allows these rails to be selectively oriented at alternate positions along the board.

Yet still another object of the present invention is to provide for a first rail assembly which is removably attached to the board.

Yet still another object of the present invention is to provide for a second rail assembly which is intended to remain spaced from the first rail. The second rail is adapted to be placed in parallel with the foot of the patient, having a "Y"-shape which includes a bifurcated portion which is angularly offset from the main portion of the rail.

Yet still another object of the present invention is to provide a plurality of pins which are removably connected to the board and rail apertures. These pins are intended to connect the board and rails via the board and rail apertures.

Yet still another object of the present invention is to provide fasteners which are intended for use with the integral anchors of the rails. These fasteners are intended to be slidably inserted through corresponding anchors, such that the fasteners intersect a metatarsal portion of the patient's foot.

Yet still another object of the present invention is to provide a method of utilizing the device in a way which allows a user to quickly, easily, and adaptably employ the device for purposes of achieving a neutral position for both foot and lower leg when in a sitting position in a manner that aids and accelerates the post-surgical recovery process.

Further objects and advantages of the present invention will become apparent from a consideration of the drawings and ensuing description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 1 is a perspective view of a lower leg and foot stabilizer 10, according to a preferred embodiment of the present invention;

FIG. 3a is a side view of a first rail 30, according to a preferred embodiment of the present invention;

FIG. 3b is a bottom view of the first rail 30, according to a preferred embodiment of the present invention;

Figure 2A:
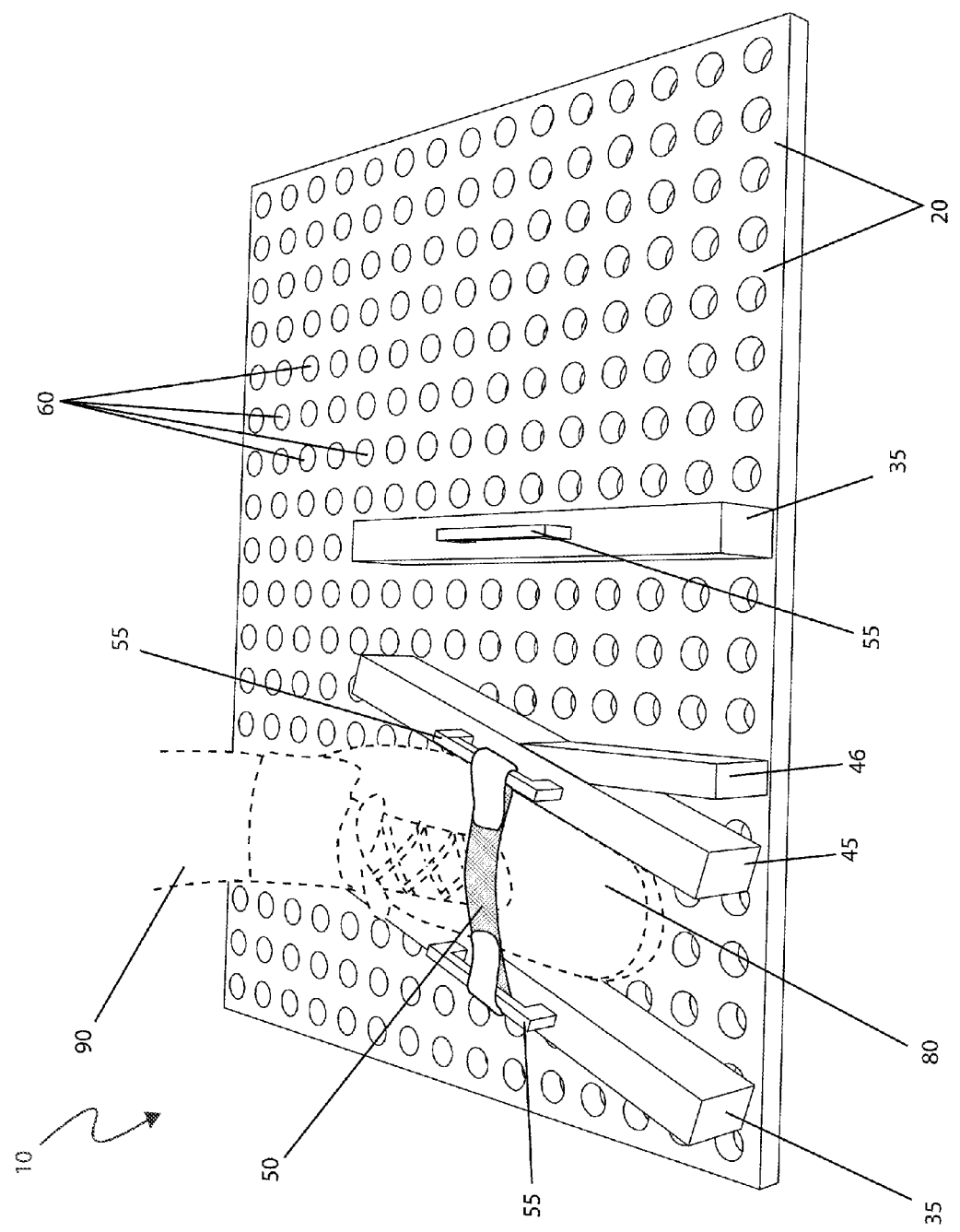
FIG. 2a is an environmental in-use view of the lower leg and foot stabilizer 10, according to a preferred embodiment of the present invention.

DESCRIPTIVE KEY 10 lower leg and foot stabilizer
20 board
30 first rail embodiment
35 first rail
40 second rail embodiment
45 second rail
46 bifurcated portion
50 hook-and-loop fastener
55 anchor
60 board aperture
65 rail aperture
70 pin
80 foot
90 lower leg

DETAILED DESCRIPTION OF THE PREFERRED EMBODIMENT

The best mode for carrying out the invention is presented in terms of its preferred embodiment, herein depicted within FIGS. 1 through 4b. However, the invention is not limited to the described embodiment and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention describes a device and method for a lower leg and foot stabilizer (herein described as the "apparatus") 10, which provides a means for holding a patient's foot 80 and lower leg 90 in a stable neutral position, thereby preventing contracture of muscles and accelerating a post-surgery healing process. Said apparatus 10 comprises a board 20, a pair of first rail embodiments 30, a second rail embodiment 40, a hook-and-loop fastener 50, a plurality of board apertures 60, a plurality of rail apertures 65, and a plurality of pins 70. One (1) first rail embodiment 30 and the second rail embodiment 40 are both utilized in conjunction to support the side portions of a patient's foot 80 and the apparatus 10 accommodates either the right or left foot 80. This adaptable apparatus 10 is an alternative to other prosthetic devices which may cause pain and discomfort to the patient.

Referring now to FIG. 1, a perspective view of the apparatus 10 and FIG. 2a, an environmental view of the apparatus 10, according to the preferred embodiment of the present invention, are disclosed. The apparatus 10 comprises a board 20, thereby providing a platform means for placing and positioning of the patient's feet 80 and thereto insert an appropriate rail embodiment 30, 40. The board 20 is intended to be placed on a level ground surface while the patient is in a sitting position. The board 20 is fabricated from a plastic material in an injection mold process and is approximately one-eighth (⅛) of an inch to one-forth (¼) of an inch thick, thereby allowing the patient to place the apparatus 10 beneath a chair firmly securing it while in use or placing the apparatus 10 it in front of the chair while in use. Said board 20 is also appropriate length and width dimensions for adaptability to a variety of sized feet 80 and situations.

The board 20 comprises a plurality of board apertures 60, thereby providing the rail embodiments 30, 40 with an insertion means. Said board apertures 60 are evenly spaced in a matrix of columns and rows at right angles on an entire top portion of the board 20, thereby providing a variety of foot 80 positions for the patient to utilize. Said board apertures 60 are approximately a half-of-an-inch (½) in diameter and are appropriate depths thereto partially accept a desired amount of user inserted pins 70 (see FIGS. 3a and 4a).

Figure 2B:
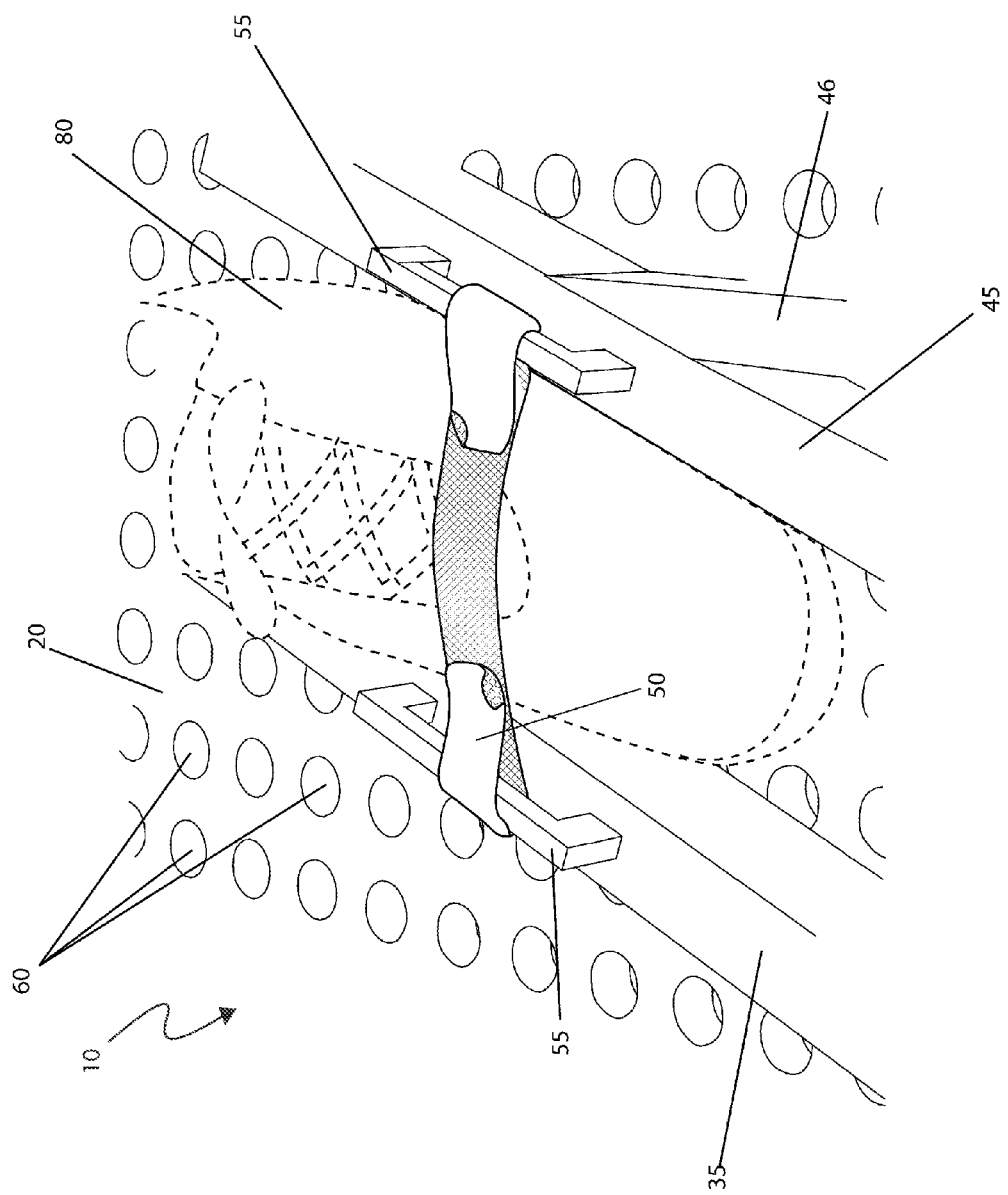
FIG. 2b is a close-up in-use view of hook-and-loop fastener 50, according to a preferred embodiment of the present invention.

Referring now to FIG. 2b, a close-up view of hook-and-loop fastener 50, according to the preferred embodiment of the present invention, is disclosed. The apparatus 10 comprises a common removably attachable hook-and-loop fastener 50 and each rail embodiment 30, 40 comprises an integral anchor 55. The hook-and-loop fastener 50 and anchors 55 operate collectively, thereby providing a securing means for the patient's foot 80 to the board 20. Each end portion of the common hook-and-loop fastener 50 is slidably inserted therethrough an anchor 55, thereby intersecting a metatarsal portion of the foot 80. Said hook-and-loop fastener 50 preferably utilizes two (2) anchors 55 for proper securing means. The anchors 55 are "U"-shaped fasteners and are preferably attached to an intermediate top location of each rail embodiment 30, 40 therein a plastic injection mold process, yet other attachment means may be incorporated such as, but not limited to: adhesives, bolts and nuts, or the like.

Referring now to FIG. 3a, a side view of the first rail embodiment 30 and FIG. 3b, a bottom view of the first rail 30 embodiment, according to the preferred embodiment of the present invention, are disclosed. The apparatus 10 comprises a pair of first rail embodiments 30, thereby providing a straight bracing means thereto the patient's foot 80 and/or lower leg 90. A top portion of the first rail 35 comprises the abovementioned anchors 55 and a bottom portion comprises a plurality of rail apertures 65. Said rail apertures 65 provide a mating means therewith a desired amount of pins 70 and the board 20. The mating means is accomplished therewith interference fitting at least two (2) pins 70 thereinto the rail apertures 65. After an appropriate amount of pins 70 are mated thereto said first rail 35 then the first rail embodiment 30 is mated thereto a desired portion of the board 20, parallel to the patient's foot 80, by means of the board apertures 60. The first rail 35 is approximately one (1) to two (2) inches in height and is preferably a variety of lengths, thereby providing usage to patients therewith a variety of sized feet 80. The first rail embodiment 30 is fabricated from a plastic material similar thereto the abovementioned board 20.

Figure 4A:
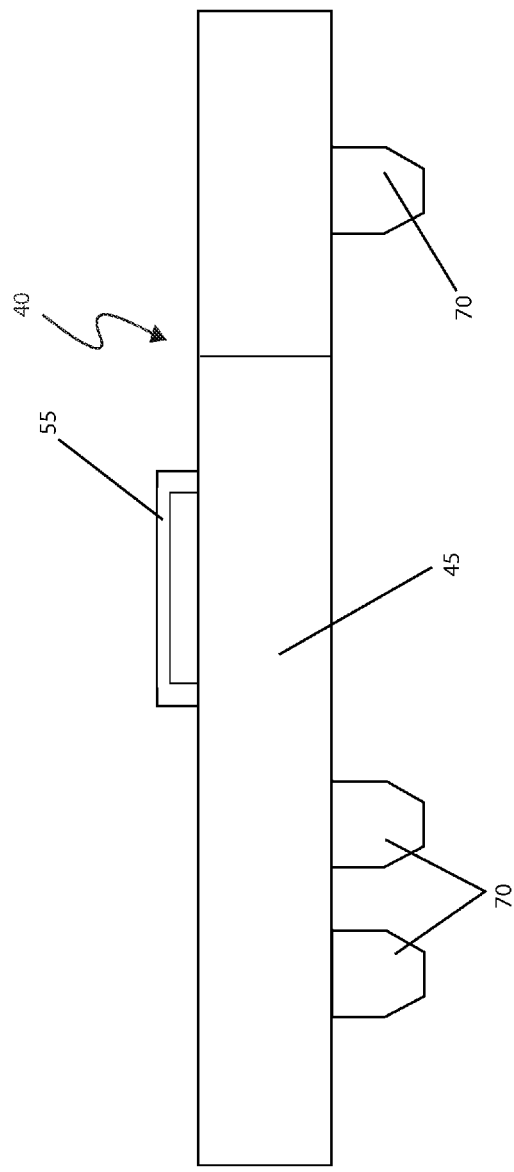
FIG. 4a is a side view of a second rail 40, according to a preferred embodiment of the present invention; and, FIG. 4b is a bottom view of the second rail 40, according to a preferred embodiment of the present invention.
Figure 4B:
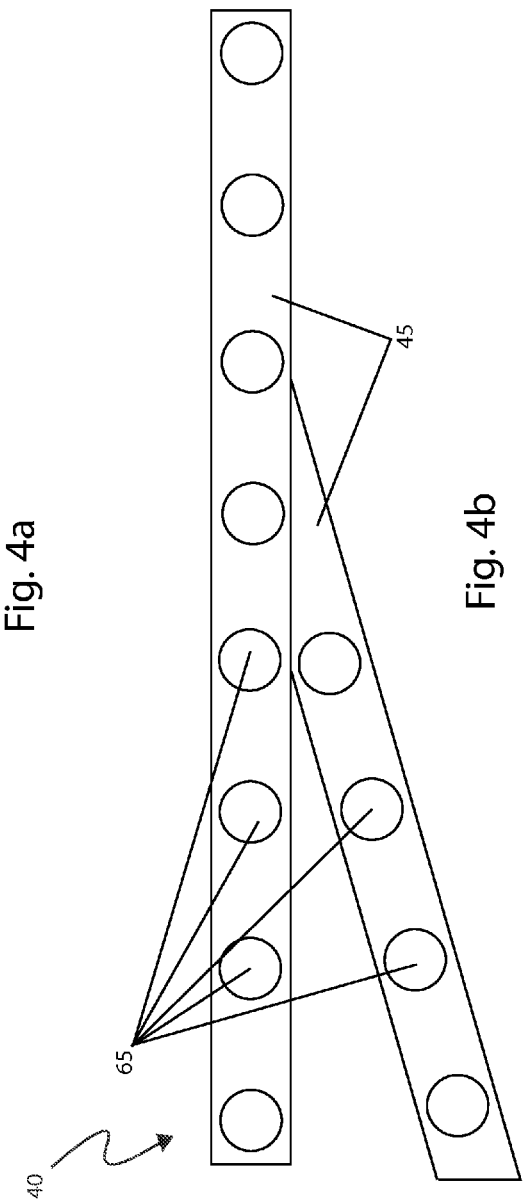

Referring now to FIG. 4a, a side view of the second rail embodiment 30 and FIG. 4b, a bottom view of the second rail embodiment 30, according to the preferred embodiment of the present invention, are disclosed. The apparatus 10 comprises a second rail embodiment 40, thereby providing another positioning means for the patient's foot 80 and lower leg 90. Similarly to the first rail embodiment 30, a top portion of a second rail 45 comprises an intermediately located anchor 55, a bottom portion comprises a plurality of rail apertures 65, and it is placed in parallel therewith the patient's foot 80. In contrast to the first rail embodiment 30, the second rail embodiment 40 is "Y"-shaped, comprising a bifurcated portion 46 which allows for a slightly angled positioning means for the patient foot 80 and lower leg 90. At least two (2) pins 70 are utilized for mating and securing the second rail 45 and bifurcated portion 46 thereto the board 20. The second rail 45 and bifurcated portion 46 are also preferably one (1) inch to two (2) inches in height, constructed in a variety of lengths thereto fit a variety of sized feet 80, and fabricated from a plastic material similar thereto the board 20

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the apparatus 10, it would be installed as indicated in FIGS. 1 and 2.

The method of installing and utilizing the apparatus 10 may be achieved by performing the following steps: acquiring the apparatus 10; placing the board 20 on a flat level surface at the foot 80 location of a patient while in a sitting position; placing a desired foot 80 thereon the board 20; inserting an appropriate amount of pins 70 thereinto the rail apertures 65 of a desired rail embodiment 30, 40; aligning the appropriate rail embodiments 30, 40 against one (1) side portion of the patients foot 80; inserting the pre-pinned 70 embodiments 30, 40 thereinto the board apertures 60, thereby mating the pins 70 and the board apertures 20; inserting an appropriate amount of pins 70 thereinto another embodiment 30, 40; aligning the embodiment 30, 40 against the patients foot 80 on the opposite side of the previously installed embodiment 30, 40; inserting and fastening one (1) end portion of the hook-and-loop fastener 50 therethrough an anchor 55 on a previously inserted embodiment 30, 40; inserting and fastening an opposite end of the fastener 50 therethrough the opposite anchor 55 and securing the foot 80 to the board 20; remaining in the secure position for a desired amount of time; unfastening the hook-and-loop fastener 50; removing the rail embodiments 30, 40 from the board 20; removing the patients foot 80 from the board 20; repeating if necessary and/or repeating with the opposite foot 80; and, eliminating pain and discomfort from the patient.

An alternative embodiment of the present invention 10 comprises an undersized version thereto accommodate wheelchairs.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A lower leg and foot stabilizer for preventing muscle contracture and thereby accelerating a post-surgery healing process while a patient is seated, said lower leg and foot stabilizer comprising:
   a board adapted to be placed on a ground surface while said patient is seated, said board further being adapted to receive a foot of said patient thereon, said board including a plurality of board apertures formed therein;
   a plurality of rails removably attached to said board, each of said rails including an integral anchor connected thereto, each of said rails having a plurality of rail apertures formed therein;
   a plurality of pins removably connected to said rail apertures and said board apertures for attaching said rails to said board; and,
   at least one fastener engaged with said anchors, said fastener being adapted to span over said foot of said patient;
   wherein said rails comprise:
      a pair of first rails removably attached to said board; and,
      a second rail removably attached to said board;
   wherein said second rail remains spaced from said pair of first rails respectively;
   wherein a top portion of said second rail includes corresponding ones of said anchors intermediately located therealong and a bottom portion of said second rail includes corresponding ones of said rail apertures;
   wherein said second rail is adapted to be placed in parallel with said foot of said patient, said second rail having a "Y"-shape including a bifurcated portion angularly offset from a main portion of said second rail;
   wherein one of said first rails is oriented parallel with said main portion of said second rail such that said bifurcated portion of said second rail extends outwardly and away from said one first rail;
   wherein one of said fasteners remains located entirely above said one first rail and said second rail while connected to said anchors.

2. The lower leg and foot stabilizer of claim 1, wherein said board apertures are evenly spaced in a matrix of columns and rows across a top portion of said board so that said rails are selectively oriented at alternate positions along said board.

3. The lower leg and foot stabilizer of claim 1, wherein an end portion of said fastener is slidably inserted through a corresponding one of said anchors such that said fastener is adapted to intersect a metatarsal portion of said foot of said patient.

4. The lower leg and foot stabilizer of claim 1, wherein said anchors are "U"-shaped and attached to an intermediate top location of each of said rails respectively.

5. The lower leg and foot stabilizer of claim 1, wherein said pair of first rails are straight and are adapted to be linearly braced against said foot of said patient.

6. The lower leg and foot stabilizer of claim 1, wherein a top portion of said pair of first rails includes corresponding ones of said anchors and a bottom portion of said pair of first rails includes corresponding ones of said rail apertures.

7. A lower leg and foot stabilizer for preventing muscle contracture and thereby accelerating a post-surgery healing process while a patient is seated, said lower leg and foot stabilizer comprising:
   a board adapted to be placed on a ground surface while the patient is seated, said board further being adapted to receive a foot of said patient thereon, said board including a plurality of board apertures formed therein;
   a plurality of rails removably attached to said board, each of said rails including an integral anchor connected thereto, each of said rails having a plurality of rail apertures formed therein;
   a plurality of pins removably connected to said rail apertures and said board apertures for attaching said rails to said board; and,
   at least one fastener engaged with said anchors, said fastener being adapted to span over said foot of said patient;

wherein said rails are adapted to be positioned at opposite sides of said foot of said patient for prohibiting undesirable movement of said foot of said patient while said foot of said patient is positioned on said board;

wherein said rails comprise:
  a pair of first rails removably attached to said board; and,
  a second rail removably attached to said board;

wherein said second rails remain spaced from said pair of first rails respectively;

wherein a top portion of said second rail includes corresponding ones of said anchors intermediately located therealong and a bottom portion of said second rail includes corresponding ones of said rail apertures;

wherein said second rail is adapted to be placed in parallel with the patient foot, said second rail having a "Y"-shape including a bifurcated portion angularly offset from a main portion of said second rail;

wherein one of said first rails is oriented parallel with said main portion of said second rail such that said bifurcated portion of said second rail extends outwardly and away from said one first rail; and, wherein one of said fasteners remains located entirely above said one first rail and said second rail while connected to said anchors.

8. The lower leg and foot stabilizer of claim 7, wherein said board apertures are evenly spaced in a matrix of columns and rows across a top portion of said board so that said rails are selectively oriented at alternate positions along said board.

9. The lower leg and foot stabilizer of claim 7, wherein an end portion of said fastener is slidably inserted through a corresponding one of said anchors such that said fastener is adapted to intersect a metatarsal portion of said foot of said patient.

10. The lower leg and foot stabilizer of claim 7, wherein said anchors are "U"-shaped and attached to an intermediate top location of each of said rails respectively.

11. The lower leg and foot stabilizer of claim 7, wherein said pair of first rails are straight and are adapted to be linearly braced against said foot of said patient.

12. The lower leg and foot stabilizer of claim 7, wherein a top portion of said pair of first rails includes corresponding ones of said anchors and a bottom portion of said pair of first rails includes corresponding ones of said rail apertures.

13. A method of installing and utilizing a lower leg and foot stabilizer for preventing muscle contracture and thereby accelerating a post-surgery healing process while a patient is seated, said lower leg and foot stabilizer including a board having a plurality of board apertures formed therein, a plurality of rails removably attached to said board, each of rails including an integral anchor connected thereto, each of said rails having a plurality of rail apertures formed therein, a plurality of pins removably connected to said rail apertures and said board apertures for attaching said rails to said board, and at least one fastener engaged with said anchors, said fastener being adapted to span over said foot of said patient, wherein said rails are adapted to be positioned at opposite sides of said foot of said patient for prohibiting undesirable movement of said foot of said patient while said foot of said patient is positioned on said board, said method comprising the steps of:

acquiring said lower leg and foot stabilizer;
  placing said board on a flat level surface while said patient is in a sitting position;
  placing said foot of said patient said board;
  inserting a first group of said pins into said rail apertures of a first one of said rails;
  aligning said rails against one side portion of said foot of said patient;
  inserting said rail pins into said board apertures;
  inserting a second group of said rail pins into said rail apertures of a second one of said rails;
  aligning said second rail on an opposite side portion of said foot of said patient;
  inserting and fastening said fastener through said anchors at each of said first and second rails; and,
  maintaining said foot of said patient in a secure position for a desired amount of time;

wherein said rails comprise:
  a pair of first rails removably attached to said board; and,
  a second rail removably attached to said board;

wherein said second rails remain spaced from said pair of first rails respectively;

wherein a top portion of said second rail includes corresponding ones of said anchors intermediately located therealong and a bottom portion of said second rail includes corresponding ones of said rail apertures;

wherein said second rail is adapted to be placed in parallel with the patient foot, said second rail having a "Y"-shape including a bifurcated portion angularly offset from a main portion of said second rail;

wherein one of said first rails is oriented parallel with said main portion of said second rail such that said bifurcated portion of said second rail extends outwardly and away from said one first rail; and, wherein one of said fasteners remains located entirely above said one first rail and said second rail while connected to said anchors.

\* \* \* \* \*